United States Patent
Boos et al.

(10) Patent No.: US 11,447,737 B2
(45) Date of Patent: Sep. 20, 2022

(54) APPARATUS AND METHOD FOR A LYSIS OF A SAMPLE, IN PARTICULAR FOR AN AUTOMATED AND/OR CONTROLLED LYSIS OF A SAMPLE

(71) Applicant: Curetis GmbH, Holzgerlingen (DE)

(72) Inventors: Andreas Boos, Bondorf (DE); Gerd Lüdke, Holzgerlingen (DE); Johannes Bacher, Leonberg-Warmbronn (DE)

(73) Assignee: CURETIS GMBH, Holzgerlingen (DE)

( * ) Notice: Subject to any disclaimer, the term of this patent is extended or adjusted under 35 U.S.C. 154(b) by 673 days.

(21) Appl. No.: 15/942,702

(22) Filed: Apr. 2, 2018

(65) Prior Publication Data
US 2018/0291331 A1   Oct. 11, 2018

Related U.S. Application Data

(62) Division of application No. 14/232,391, filed as application No. PCT/EP2011/003770 on Jul. 27, 2011, now Pat. No. 9,963,670.

(51) Int. Cl.
*C12M 1/00* (2006.01)
*G01N 1/28* (2006.01)
(Continued)

(52) U.S. Cl.
CPC ............. *C12M 47/06* (2013.01); *C12N 1/066* (2013.01); *G01N 1/286* (2013.01); *G01N 1/38* (2013.01);
(Continued)

(58) Field of Classification Search
CPC . C12N 1/066; G01N 1/38; G01N 1/44; G01N 1/286; G01N 2035/00524;
(Continued)

(56) References Cited

U.S. PATENT DOCUMENTS 3,770,191 A    11/1973  Blum
6,783,993 B1    8/2004  Malmquist
(Continued)

FOREIGN PATENT DOCUMENTS

JP    H02-97664    8/1990
JP    H08-82627    3/1996
(Continued)

OTHER PUBLICATIONS

Hua et al., "Study on the Extraction of Nucleic Acids from Minimal Tissue by Improved Splitting Method," *Clinical Journal of Medical Officer*, 27(3) 250022 Jinan Junior College of Medicine (1999).
(Continued)

*Primary Examiner* — Gautam Prakash
(74) *Attorney, Agent, or Firm* — Neal, Gerber & Eisenberg LLP

(57) ABSTRACT

The present invention provides an apparatus and a method for a lysis procedure, in particular for an automated and/or controlled lysis procedure of a sample, in particular a biological sample. The apparatus comprises at least one rotation disc (31), at least one vial holder (90) which is configured to receive a vial (100), wherein the vial holder (90) is arranged on the disc (31), at least one driving device (20) which is configured to rotate the disc (31) and the vial holder (90), at least one heating device (60) which is configured to heat the sample to a determined incubation temperature, and—at least one control device (70) which is configured to control the driving device (20) and/or the heating device (60) by means of a timing and/or step control, and/or—at least one transmitting device (80) for inductive coupling for energy and signal transmission, which is configured to transmit the energy for heating to the heating device (60), and/or—wherein the driving device (20) is configured to rotate the disc (31) in a first direction (A1)
(Continued)

and/or with a first speed, and to rotate the vial holder (90) in a second direction (A3) and/or with a second speed. The apparatus and the method are adapted for an (automated) lysis procedure, wherein the lysis can be carried out in a safe, efficient and effective manner.

19 Claims, 6 Drawing Sheets

(51) Int. Cl.
*G01N 1/38* (2006.01)
*G01N 1/44* (2006.01)
*C12N 1/06* (2006.01)
*G01N 35/02* (2006.01)
*G01N 35/00* (2006.01)
*G01N 35/04* (2006.01)

(52) U.S. Cl.
CPC .............. *G01N 1/44* (2013.01); *G01N 35/025* (2013.01); *G01N 2035/00504* (2013.01); *G01N 2035/00524* (2013.01); *G01N 2035/0441* (2013.01)

(58) Field of Classification Search
CPC . G01N 2035/0441; G01N 2035/00504; G01N 35/025; C12M 47/06
See application file for complete search history.

(56) References Cited

U.S. PATENT DOCUMENTS

| | | |
|---|---|---|
| 8,647,858 B2 | 2/2014 | Broyer et al. |
| 2002/0132353 A1 | 9/2002 | Tamura et al. |
| 2002/0137194 A1 | 9/2002 | Ammann et al. |
| 2005/0123445 A1* | 6/2005 | Blecka et al. ....... G01N 35/025 422/64 |
| 2006/0068492 A1 | 3/2006 | Choi et al. |
| 2006/0175443 A1* | 8/2006 | Bysouth ................ B01F 9/0001 241/30 |
| 2008/0085221 A1 | 4/2008 | Downs et al. |
| 2008/0180842 A1 | 7/2008 | Kaufmann et al. |
| 2011/0076199 A1 | 3/2011 | Meller et al. |

FOREIGN PATENT DOCUMENTS

| | | | |
|---|---|---|---|
| JP | 2002-196006 | | 1/2002 |
| JP | 2002-098704 | | 4/2002 |
| JP | 2007-147658 | | 6/2007 |
| JP | 2007-185101 | | 7/2007 |
| JP | 2011-012969 | | 1/2011 |
| JP | 2011-019488 | | 2/2011 |
| JP | 2011-045873 | | 3/2011 |
| JP | 2011-122919 | | 6/2011 |
| WO | 2011/042426 | | 4/2011 |
| WO | WO2011/042426 | * | 4/2011 |

OTHER PUBLICATIONS

European Patent Office, International Preliminary Report on Patentability for PCT/EP2011/003770 (dated Jan. 28, 2014).
European Patent Office, International Search Report for International PCT/EP2011/003770 (dated Mar. 1, 2012).

* cited by examiner

APPARATUS AND METHOD FOR A LYSIS OF A SAMPLE, IN PARTICULAR FOR AN AUTOMATED AND/OR CONTROLLED LYSIS OF A SAMPLE

TECHNICAL FIELD OF THE INVENTION

The invention relates to an apparatus and a method for a lysis of a sample, in particular for an automated and/or controlled lysis of a sample, in particular a biological sample.

BACKGROUND OF THE INVENTION

A major task in biochemical and molecular diagnostic laboratories is sample homogenization, cell and tissue lysis and the mixing of reagents. The lysis is used for subsequent isolation of biomolecules in the field of research and development, chemical analysis and diagnostics.

Today, vortexers and bead mills are routinely used to perform these tasks. Such systems agitate the fluids and sample material in a vial in such a way that the vials are accelerated and decelerated in a repetitive pattern in one or more dimensions.

For sample homogenization, beads (glass, ceramic or other materials) are added. Due to the rapid acceleration and deceleration steps, these beads generate a physical impact force on the sample material and 'grind' or 'mill' it into smallest particles that are then suspended in a surrounding fluid (hence the name 'bead milling'). On a cellular level, cell walls are cracked under such acceleration, deceleration, impact and shear forces if the bead sizes are selected appropriately. This is for example necessary for DNA tests where access to the DNA embedded in cells is needed. Besides milling with a conventional vortexer, the use of bead mills allows the milling of different materials.

There are also some known chemical agents that improve the cell opening process.

The combination of chemical or enzymatic lysis steps with mechanical milling steps additionally improves the performance of the lysis procedure. The use of chemical or enzymatical steps require certain incubation temperatures, as well as thorough mixing of the reagents during the incubation steps.

Despite the wide usage, the known vortexing and bead milling devices and procedures in many cases have low efficiency and therefore need a substantial amount of processing time. Additionally, these methods need to be combined with incubation steps at different temperatures to allow efficient lysis of a wide variety of clinical samples. The current methods require a combination of different steps involving the steps of mixing, incubation at different temperatures, ideally interrupted by e. g. bead milling. Each of the steps is performed in different instruments (vortexer, heating block, bead mill . . . ) as a combination of manual steps. That is, these sequential steps require manual work of well trained operators.

In order to avoid the time-consuming operation due to the several instruments needed for a lysis process, efforts have been made to reduce the number of the necessary devices. However, with conventional devices it is not possible to overcome for example problems caused by the high G-forces which occur due to rotation operations (several steps cannot be carried out or cannot be carried out in an appropriate manner during the rotation of the vial, for example appropriate heating and/or determining the temperature of the sample or even temperature regulation of the agitated sample).

With other known methods, the bead milling step is performed at lower temperatures. Several of the bead mills commercially available are equipped with a system which allows the sample to be milled in a refrigerated compartment of the instrument. Other systems allow for submersing the grinding beaker or vial into liquid nitrogen before bead milling, so that the process is carried out at low temperatures. However, such devices do not provide a desired degree of efficiency, especially when treating viscous biological samples.

An analysis of mechanical effects during the bead milling process shows that the efficiency mainly depends on the strength of the impact collisions of the beads with the suspended sample material and cells. Such collision forces can be increased by increasing the density of the beads, the amount of beads and/or increasing the acceleration and deceleration speed. Today's vortexers and bead mills are already at their limits with respect to acceleration and deceleration speeds due to their construction.

A typical known system does not only accelerate and decelerate the sample material and vial but also the much larger masses of the vial holders. Furthermore the movements are most often created by a rotating motor shaft driving an eccentric tappet. This eccentric tappet then drives a plate that is spring suspended for example in the x- and z-axis (that is, right and left movements, up and down movements). The plate is coupled with a vial holder or the vial is pressed on that plate manually. Due to large unbalanced masses, such movements create huge stress on the whole construction, thereby limiting the way of travel (maximum eccentricity/maximum deflection of the vial holder) and the maximum velocities that can be achieved. A typical way of travel is only a few millimeters with a maximum of 3000 to 4000 cycles per minute. To avoid that such systems start moving on the desk surface during operation, they are often equipped with a very heavy additional mass and dampers in the bottomplate.

SUMMARY OF THE INVENTION

The object or technical problem of the present invention is to provide an apparatus and a method for a lysis, in particular for an automated and/or controlled lysis of a sample, in particular a biological sample, that overcome the above described drawbacks of the conventional devices and methods. In particular, it is the object of the present invention to provide an apparatus and a method for a lysis, in particular for an automated lysis, wherein the lysis can be carried out in a safe, efficient and effective manner.

The above mentioned problems are solved by an apparatus for a lysis, in particular for an automated lysis of a sample, in particular a biological sample, and by a method for a lysis, in particular for an automated lysis of a sample, in particular a biological sample.

The present invention will now be described by defining different aspects of the invention. Each aspect so defined may be combined with any other aspect or aspects unless clearly indicated to the contrary. In particular, any feature indicated as being preferred or advantageous may be combined with any other feature or features indicated as being preferred or advantageous.

In a first aspect, the present invention relates to an apparatus for a lysis of a sample, in particular for an automated and/or controlled lysis of a sample, wherein the apparatus comprises:

- at least one rotation disc,
- at least one vial holder which is configured to receive or for receiving a vial, wherein the vial holder is arranged on the disc,
- at least one driving device which is configured to rotate or for rotating the disc and the vial holder,
- at least one heating device which is configured to heat or for heating the sample to at least one determined incubation temperature,
- at least one control device which is configured to control or for controlling the driving device and/or the heating device by means of a timing and/or step control.

It is possible to provide a cooling device for cooling the sample to at least one determined temperature. The heating and cooling process can be carried out stepwise.

The wording "apparatus for a lysis of a sample, in particular for an automated and/or controlled lysis of a sample" is interchangeable with the wording "apparatus for lysing of a sample, in particular for automated and/or controlled lysing of a sample". This applies to all aspects of the present invention.

That is, the control device comprises a timing and/or step (process or sequence) control device or function. Also a step diagram control would be possible with the appropriate components. The at least one control device is configured to control the driving device and the heating device, and/or is in communication with the driving device and the heating device, so that the driving device and the heating device operate in a coordinated manner to control the lysis (procedure). Therefore, the steps are carried out in a determined order by means of the timing and/or step control.

An essential point of the invention in accordance with the first aspect is that the automated lysis or lysis procedure (with all the necessary steps like vortexing (that is, in particular mixing), grinding, milling, heating and keeping the vial holder (and therefore the sample) in a resting phase) can be carried out without the need of a well trained operator, since the necessary steps are automatically performed by determining and/or considering the time flow and/or the course of action of the procedure. That is, the control device operates the apparatus in a manner that the driving device and the heating device work in a coordinated manner, wherein the control device "decides", due to time (timing) and/or step control (also feedback control), when the different steps of the process (heating or rotating, keeping the vial holder in a resting phase) have to be carried out. Thus, the control device starts and stops the corresponding step, and controls the subsequent use or application of different rotation speeds and/or angular velocity and incubation temperatures. That is, the apparatus operates in an automated manner and carries out the whole lysis procedure without unnecessary interruptions and/or using different devices for the procedure. Additionally, with the control device, a precise temperature regulation within the fast rotating grinding stations (vial holders) is provided (the control device allows for carrying out a feedback control).

A combination of appropriate buffers and enzymes with bead milling (in the apparatus for automated lysis of a sample) at elevated temperatures and resembling the incubation temperatures of the respective enzymes allows very efficient lysis of different sample materials with an identical protocol (that is, different sample material can be treated in the same manner).

All preferred embodiments of the second, the third and the fourth aspect can also be preferred embodiments with respect to the first aspect (see the preferred embodiments with respect to the driving device, the heating device, the control device and the transmitting device).

Preferably, the driving device comprises driving means for driving the disc, a central pin, to which the disc is pivot-mounted, a central pinion, fixed on the central pin, at least a first stage gear or gear wheel, driven via the disc by the central pinion, and at least a second stage gear or gear wheel, driven by the first stage gear. The central pin and therefore the central pinion are preferably non-rotating elements and are fixed. The sample holder is associated with the second stage gear, and the first stage gear and the second stage gear are pivot-mounted on or within the disc. The disc and the gear (at least the moveable parts of the gear) defining a rotating device or at least a part of the rotating device. Also the central pin and the central pinion can be seen as part of the rotating device, although these components do not rotate.

The gear (that is the first stage gear wheel and the second stage gear wheel) is preferably driven via the disc by the fixed pinion in the disc center. In this case, the disc is a carrier carrying the gear wheels and due to driving the disc, the gear wheels are driven correspondingly.

Preferably, the heating device comprises at least one heating sleeve (heating element) which provides the necessary incubation temperature(s). The heating sleeve preferably surrounds the vial holder and/or the second stage gear (preferably, each of the vial holders is surrounded by a heating sleeve). With the heating device a precise temperature regulation/controlling within the fast rotating vial holder is possible.

It is important to balance the thermal mass of the heating sleeve in a way that it is big enough to allow efficient and homogenous temperature transfer to the vial holder (and therefore to the sample over the vial), and small enough to allow efficient cooling down of the sample within the vial holder by convective cooling.

Preferably, the heating device comprises or is associated with a least one temperature sensor. The sensor is associated with the heating sleeve, the vial holder and/or the sample, which detects the temperature of the heating sleeve, the vial holder and/or the sample and provides a corresponding signal (temperature detecting sensor).

As already stated above, the control device is configured to control the driving device and/or the heating device, so that the driving device and the heating device operate in a coordinated manner to control the lysis procedure or lysis steps.

The control device preferably comprises a time and/or step control device or function, in particular a feedback control device, or is configured to carry out a time and/or step control, in particular a feedback control, for controlling the driving device and/or the heating device. That is, the progress or course of action of the single steps of the lysis procedure is controlled by means of the time and/or step control device or function and therefore, by means of the control device.

The control device preferably comprises a driving control device or function, and/or a timing control device or function, and/or a temperature control device or function for controlling the driving device and/or the heating device. These devices are configured to carry out the time and/or step control (the devices are in communication with the driving device and the heating device to carry out the time and/or step control).

Preferably, the control device is configured to control the driving device and/or the heating device at least in response to the signal(s) provided by the temperature sensor(s).

The control device is for examples configured as the time and/or step control device which control(s) the single steps necessary for carrying out the lysis procedure. The control device (or devices) initiates (starts) and stops the single steps at a desired or determined point of time (determines and/or adjusts the duration of the single steps), determines and/or adjusts the direction and the speed of the rotation of the components (for example of the disc) and determines and/or adjusts the temperatures which have to be achieved (incubation temperatures). Due to feedback, for example due to a measured temperature and/or due to the expiry of a required or determined time period, the course of action (the following steps) are carried out in the required manner.

With an ideal protocol (example), the following steps are for example carried out:
a) 1 minute milling the sample (rotating phase) during heating up the sample to the first determined incubation temperature, for example 56° C.;
b) 5 minutes keeping the sample unmoved (resting phase) at the first determined incubation temperature;
c) 0.5 minutes mixing the sample (rotating phase) at the first determined incubation temperature;
d) 5 minutes keeping the sample unmoved (resting phase) at the first determined incubation temperature;
e) heating up the sample (resting phase) to the second determined incubation temperature, for example 96° C.;
f) 5 minutes milling the sample (rotating phase) at the second determined incubation temperature;
g) 10 minutes keeping the sample unmoved (resting phase) at the second determined incubation temperature;
h) 0.5 minutes cooling down the sample.

A rotating phase is performable or can be carried out for a determined time period. A resting phase is a phase in which no rotation is carried out, that is, an unmoved phase or a phase without any movement or without a rotation is provided. Also the resting phase is performable or can be carried out for a determined time period. The time periods are controlled by the control device.

Preferably, the step of rotating comprises rotating the disc in a first direction and rotating the vial holder in a second direction, opposite to the first direction, and while the disc performs one rotation, the vial holder performs one rotation in the opposite direction, thus always or substantially keeping the absolute orientation of the vial holder substantially constant while rotating.

The lysis can be carried out for example as follows (as an example for the steps a) and b)):

When starting the lysis procedure, the driving device starts (the rotation of the disc) and for example, the driving control device controls the driving device with respect to the direction of rotation of the disc and with respect to the speed, and the timing control device controls the driving device with respect to the duration of the rotating phase of step a). Additionally, the heating device starts and the temperature control device controls the heating device, and therefore, the temperature of the sample (by means of the temperature sensor, that is monitoring the temperature).

The timing control device provides an output signal upon expiry of the time period of step a) for stopping the driving device (feedback control by means of monitoring the duration of the time period). The temperature control device provides an output signal upon receiving a corresponding signal from the temperature sensor that the determined incubation temperature has been reached (feedback control by means of the signals provided by the temperature sensor).

Then, the next step, step b) can be triggered. The timing control device thus controls the driving device (resting phase for 5 minutes) and provides an output signal upon expiry of this time period. The heating device will be controlled to keep the incubation temperature (for example 56° C.). After expiry of the time period of step b), the next step, step c) can be triggered etc. The heating device is configured to control the temperature during a rotating phase and/or during a resting phase.

Preferably, the driving device comprises a planetary gear. That is, the at least first stage gear(s) and the second stage gear(s) are arranged as part of the planetary gear. The planetary gear allows the drive of the disc and the vial holders to be performed in an efficient manner. Additionally, a planetary gear is small in size and thus, the apparatus can be provided as a compact device.

Preferably, the driving device is configured
to rotate the disc in a first direction and/or with a first speed and/or (angular) velocity, and
to rotate the vial holder in a second direction, and/or with a second speed and/or (angular) velocity.

Preferably, the driving device is configured
to rotate the disc in a first direction and/or with a first speed and/or (angular) velocity, and
to rotate the vial holder in a second direction, opposite to the first direction, and/or with a second speed and/or (angular) velocity.

In principle, it is possible to rotate the disc and the vial holder in the same direction (that is, the first direction is equal to the second direction; it is also possible that the first speed is equal to the second speed). However, the best results are achieved when the vial holder rotates relative to the disc.

Preferably, the driving device is configured to rotate the disc and the vial holder such that or in such a manner that the absolute orientation of the vial holder is kept constant while rotating. That is, the absolute orientation of the vial holder is always kept constant while rotating.

More preferably, the driving device is configured
to rotate the disc in a first direction and/or with a first speed and/or (angular) velocity, and
to rotate the vial holder in a second direction, opposite to the first direction, and/or with a second speed and/or (angular) velocity,
and while the disc performs one rotation, the vial holder performs one rotation in the opposite direction, thus (always) keeping the absolute orientation of the vial holder substantially constant while rotating.

Experimental work showed that further increasing acceleration and deceleration (heavy deceleration) as well as larger movements substantially increase efficiency of the bead milling effect. The invention overcomes the major problems as described above by avoiding any unbalanced mass in the system (like in a vortexer), although for example mixing, milling and grinding steps (that is, also "shaking" steps) are carried out and acceleration is increased. The vial holders, for example two or more, are equally spaced on a circle on the rotating disc.

The specific type of movement (for example by means of the planetary gear, which allows for moving the disc and the vial holder in a desired direction, for example in opposite directions) allows for carrying out all necessary steps for a lysis procedure, that is, vortexing, grinding, and milling the sample. Conventional vortexers merely allow for "shaking", that is mixing the sample, however no further steps (like heating) can be carried out. Additionally, vortexers do not run smooth due to the eccentric arrangement and therefore, there are limitations with respect to the rotation speed (acceleration). The individual movement of the disc and the vial holder in accordance with the present invention allows for carrying out the necessary steps in a very efficient manner (smooth running, high rotation speeds and therefore, high efficiency).

Preferably the disc is equipped with at least two vial holders. This allows for easily balancing the system and avoiding any mass imbalances. In case of only one vial holder the system can be easily balanced by adding an additional mass with the same weight and distribution as the gear. In a preferred configuration, for example four first stage gears and four second stage gears are provided on or within the disc and rotating around the central pinion.

Preferably, and as already mentioned above (and this is a very effective manner), the two stage gears (or for example a two stage gear chain) coupled to the center pinion drive the individual vial holder(s) in such a way that while the rotation disc performs one rotation, the vial holder(s) perform(s) one rotation in the opposite direction, thus always and/or substantially keeping the absolute orientation of the vial holder(s) substantially constant while rotating (balanced masses, for example in comparison with a conventional vortexer). That is, the driving device rotates the disc in a first direction, and the vial holder(s) in a second direction, opposite to the first direction, preferably with the same angular velocity. This is in contrast to a conventional vortexer with the eccentric movements and in contrast to a conventional centrifuge (which does not allow for any "shaking" steps) with fixed coupled vial holders, coupled to the rotating disc. Such a system without a gear only creates a constant centripetal force pressing the sample and fluids constantly outwards.

The first stage gear rotate for example clockwise and the second stage gear—and thus also the vial holders—rotate anti-clockwise. As the gear ratio overall is preferably 1:1, the vial holders rotate anti-clockwise with the same angular velocity as the disc rotates clockwise. As a consequence, the vial holders while moving on a circular track do not make any rotational movements themselves referred to e.g. the fixed footplate or bottom side and center pin.

The effective movement is a superimposition of at least two circular movements. The samples contained in the vials in the vial holders effectively are moved left/right and for- and backwards. The frequency is identical to the rotation speed of the disc.

Additionally, due to the possibility to rotate the disc as well as the vial holder or the vial holders (individual rotation of disc and vial holder, realized by the driving device, in particular by means of the planetary gear or arrangement) in a specific manner, the arrangement runs smoothly and with low vibrations, since the specific movement (rotation) of the components (disc, vial holder) allows for harmonizing mass imbalances, although mixing, milling and grinding steps are carried out. That is, due to the arrangement of the components of the apparatus and the specific possibility of moving the components (disc, vial holder) by means of the driving device, a system with balanced masses is obtained. In other words, the eccentric motion or movement (necessary for example in a vortexer) is converted into rotation, thus, the strong acceleration forces do not longer act on the mechanical components.

The individual rotation of the disc and the vial holder or vial holders means that the disc and the holders are rotatable in different directions (clockwise or counterclockwise) and with different speeds, depending for example on the gear ratio. However, rotation of the components in the same manner (in the same direction and/or with the same speed) is also possible. Also a rotation of the components independently from one another is possible, with a driving device providing different driving means. However, it is the intention to rotate the components in such a manner that a balanced system is provided.

If e. g. the second stage gear has more teeth or fewer teeth than the center fixed pinion, the vial holders in addition perform a rotational movement superimposed to the original movement with a rotational speed determined by the ratio of the number of teeth of the pinions. That is, if the number of teeth of the central pinion (inner pinion) and the second stage gear (outer pinion) in the gear are not equal, the vial holders in addition perform a rotational movement that can help improve mixing of fluids in the vials. These rotations (for example superimposed slow rotation) can be adjusted easily by selecting the appropriate teeth ratio of the inner and outer pinion.

Due to the balanced masses of such a system, the rotation speed can be easily increased compared to the current systems. The remaining imbalance of masses can only origin from the sample material and volumes itself. With typical sample volumes of a few milliliters, such imbalances can only be in the order of a few grams maximum. This can be tolerated by the inventive device up to several thousand rpm (rounds per minute).

As the maximum acceleration/deceleration is proportional to the radius and proportional to the square of the rotational speed of the disc, improvements with respect to the diameter of the disc and the rotation speed compared to the known vortexing devices in the order of 40 are easily achievable (e.g. ten times the radius—e.g. 5 mm vs. 5 cm—and twice the speed—3000 rpm vs. 6000 rpm).

Also more discs can be provided, for example staggered, to increase the number of available vial holders for high sample throughput applications.

The apparatus preferably comprises at least one transmitting device for inductive coupling for energy and/or signal transmission (transmitting device, transmitting device for transmitting energy and/or signals), which is configured
  to at least transmit the energy for heating to the heating device, and/or
  to at least transmit the signal(s) provided by the temperature sensor to the control device.

The energy for heating the heating device, that is, the sleeve, is preferably transmitted by means of the transmitting device (means for inductive coupling for energy and signal transmission, inductive transducer). The heating device is for example formed as a resistance heating device. It is also possible to use a Peltier element or similar devices.

Preferably, the signal(s) provided by the temperature sensor are also transmitted by the transmitting device (also for example the energy for the sensor). That is, the values, measured by the sensor are for example transmitted to the control device, and thus, the time and/or step control is carried out accordingly. This allows for an easy way of transmission, without the need of cable, wires or the like. The construction of a bead milling device containing a heatable vial holder is very complex, due to the high rotation speed of the mill, especially within a planetary bead mill, since there are two rotation axes. However, the use of the inductive transducer allows for carrying out the necessary lysis steps without the need of using different devices. The transmission of energy and signals does not interfere with the rotation of the disc and the vial holders.

Due to the cooperation of the control device, the driving device, the heating device and the sensor(s), an automated lysis procedure can be carried out. The transfer of energy and of measurement signals of a temperature probe only has to take place over one rotation axis instead of two.

In a second aspect, the present invention relates to an apparatus for a lysis of a sample, in particular for an automated and/or controlled lysis of a sample, wherein the apparatus comprises:
- at least one rotation disc,
- at least one vial holder which is configured to receive or for receiving a vial, wherein the vial holder is arranged on the disc,
- at least one driving device which is configured to rotate or for rotating the disc and the vial holder,
- at least one heating device which is configured to heat or for heating the sample to at least one determined incubation temperature,
- wherein the driving device is configured
  - to rotate the disc in a first direction and/or with a first speed, and
  - to rotate the vial holder in a second direction and/or with a second speed.

An essential point of the invention in accordance with the second aspect is in particular to provide a system with balanced masses, as described with respect to the first aspect. That is, the apparatus allows for mixing the sample (like in a conventional vortexing device) and additionally, the system runs in a smooth manner (balanced masses, see first aspect). The inventive apparatus runs in a smooth manner (like a conventional centrifuge), although steps are carried out which are usually carried out by means of a vortexer (vortexing device).

All preferred embodiments of the first, the third and the fourth aspect can also be preferred embodiments with respect to the second aspect (see the preferred embodiments with respect to the driving device, the heating device, the control device and the transmitting device). As to the further explanations and information with respect to these embodiments (below), it is referred to the explanations and information provided above with respect to the first aspect of the invention.

Preferably, the driving device comprises:
- driving means for driving the disc,
- a central pin, to which the disc is pivot-mounted,
- a central pinion, fixed on the central pin,
- at least a first stage gear, driven via the disc by the central pinion,
- at least a second stage gear, driven by the first stage gear, wherein the vial holder is associated with the second stage gear.

Preferably, the driving device comprises a planetary gear. That is, the first stage gear(s) and the second stage gear(s) are arranged as part of the planetary gear.

Preferably, the driving device is configured to rotate the disc and the vial holder such that or in such a manner that the absolute orientation of the vial holder is kept constant while rotating.

Preferably, the driving device is configured
- to rotate the disc in a first direction and/or with a first speed, and
- to rotate the vial holder in a second direction, opposite to the first direction, and/or with a second speed,
- and while the disc performs one rotation, the vial holder performs one rotation in the opposite direction, thus keeping the absolute orientation of the vial holder substantially constant while rotating. That is, the absolute orientation of the vial holder is always kept constant while rotating.

Preferably, the heating device comprises at least one heating sleeve surrounding the vial holder and/or the second stage gear.

Preferably, the heating device comprises or is associated with a least one temperature sensor associated with the heating sleeve, the vial holder and/or the sample, which detects the temperature of the heating sleeve, the vial holder and/or the sample and provides a corresponding signal.

Preferably, the apparatus comprises at least one control device which is configured to control or for controlling the driving device and/or the heating device by means of a timing and/or step control. That is, the control device comprises a timing and/or step control device or function.

The at least one control device is configured to control the driving device and/or the heating device, so that the driving device and the heating device operate in a coordinated manner to control the lysis (procedure). Therefore, the steps are carried out in a determined order by means of the timing and/or step control.

Preferably, the control device comprises a driving control device or function, and/or a timing control device or function, and/or a temperature control device or function for controlling the driving device and/or the heating device.

Preferably, the control device is configured to control the driving device and/or the heating device at least in response to the signal(s) provided by the temperature sensor(s).

Preferably the apparatus comprises at least one transmitting device for inductive coupling for energy and signal transmission, which is configured
- to transmit the energy for heating to the heating device, and/or
- to transmit the signal(s) provided by the temperature sensor to the control device.

In a third aspect, the present invention relates to an apparatus for a lysis of a sample, in particular for an automated and/or controlled lysis of a sample, wherein the apparatus comprises:
- at least one rotation disc,
- at least one vial holder which is configured to receive a vial, wherein the vial holder is arranged on the disc,
- at least one driving device which is configured to rotate the disc and the vial holder,
- at least one heating device which is configured to heat the sample to at least one determined incubation temperature,
- at least one transmitting device for inductive coupling for energy and/or signal transmission, which is configured to transmit the energy for heating to the heating device.

An essential point of the invention in accordance with the third aspect is in particular that at least the energy and/or the signals are transmitted in an easy manner, wherein no wires or the like are needed. The transmission of energy and signals does not interfere with the rotation of the disc and the vial holders.

All preferred embodiments of the first, the second and the fourth aspect can also be preferred embodiments with respect to the third aspect (see the preferred embodiments with respect to the driving device, the heating device, the control device and the transmitting device). As to the further explanations and information with respect to these embodiments (below), it is referred to the explanations and information provided above with respect to the first aspect of the invention.

Preferably, the driving device comprises:
driving means for driving the disc,
a central pin, to which the disc is pivot-mounted,
a central pinion, fixed on the central pin,
at least a first stage gear, driven via the disc by the central pinion,
at least a second stage gear, driven by the first stage gear, wherein the vial holder is associated with the second stage gear.

Preferably, the driving device comprises a planetary gear. That is, the first stage gear(s) and the second stage gear(s) are arranged as part of the planetary gear.

Preferably, the driving device is configured
to rotate the disc in a first direction and/or with a first speed, and
to rotate the vial holder in a second direction and/or with a second speed.

Preferably, the driving device is configured to rotate the disc and the vial holder such that or in such a manner that the absolute orientation of the vial holder is kept constant while rotating.

Preferably, the driving device is configured
to rotate the disc in a first direction and/or with a first speed, and
to rotate the vial holder in a second direction, opposite to the first direction, and/or with a second speed,
and while the disc performs one rotation, the vial holder performs one rotation in the opposite direction, thus always keeping the absolute orientation of the vial holder substantially constant while rotating.

Preferably, the heating device comprises at least one heating sleeve surrounding the vial holder and/or the second stage gear.

Preferably, the heating device comprises or is associated with a least one temperature sensor associated with the heating sleeve, the vial holder and/or the sample, which detects the temperature of the heating sleeve, the vial holder and/or the sample and provides a corresponding signal.

Preferably, the apparatus comprises at least one control device which is configured to control or for controlling the driving device and/or the heating device by means of a timing and/or step control. That is, the control device preferably comprises a timing and/or step control device or function.

The at least one control device is configured to control the driving device and/or the heating device, so that the driving device and the heating device operate in a coordinated manner to control the lysis (procedure). Therefore, the steps are carried out in a determined order by means of the timing and/or step control.

Preferably, the control device comprises a driving control device or function, and/or a timing control device or function, and/or a temperature control device or function for controlling the driving device and/or the heating device.

Preferably, the control device is configured to control the driving device and/or the heating device at least in response to the signal(s) provided by the temperature sensor(s).

Preferably, the transmitting device for inductive coupling for energy and/or signal transmission is configured to transmit the signal(s) provided by the temperature sensor to the control device.

In a fourth aspect, the present invention relates to an apparatus for a lysis of a sample, in particular for an automated and/or controlled lysis procedure of a sample, in particular a biological sample. The apparatus comprises at least one rotation disc,
at least one vial holder which is configured to receive a vial, wherein the vial holder is arranged on the disc,
at least one driving device which is configured to rotate the disc and the vial holder,
at least one heating device which is configured to heat the sample to at least one determined incubation temperature,
and
at least one control device which is configured to control the driving device and/or the heating device by means of a timing and/or step control, and/or
at least one transmitting device for inductive coupling for energy and/or signal transmission, that is for inductive coupling of energy and/or signals, which is configured to transmit the energy for heating to the heating device, and/or
wherein the driving device is configured to rotate the disc in a first direction and/or with a first speed, and to rotate the vial holder in a second direction and/or with a second speed.

All preferred embodiments of the first, the second and the third aspect can also be preferred embodiments with respect to the fourth aspect (see the preferred embodiments with respect to the driving device, the heating device, the control device and the transmitting device). As to the further explanations and information with respect to these embodiments (below), it is referred to the explanations and information provided above with respect to the first aspect of the invention.

The apparatus contains all essential points or qualities of the aspects as described above.

Preferably, the driving device comprises:
driving means for driving the disc,
a central pin, to which the disc is pivot-mounted,
a central pinion, fixed on the central pin,
at least a first stage gear, driven via the disc by the central pinion,
at least a second stage gear, driven by the first stage gear, wherein the vial holder is associated with the second stage gear.

Preferably, the driving device comprises a planetary gear. That is, the first stage gear(s) and the second stage gear(s) are arranged as part of the planetary gear.

Preferably, the driving device is configured
to rotate the disc in a first direction and/or with a first speed and/or (angular) velocity, and
to rotate the vial holder in a second direction, opposite to the first direction, and/or with a second speed and/or (angular) velocity.

Preferably, the driving device is configured to rotate the disc and the vial holder such that or in such a manner that the absolute orientation of the vial holder is kept constant while rotating.

Preferably, the driving device is configured
to rotate the disc in a first direction and/or with a first speed, and
to rotate the vial holder in a second direction, opposite to the first direction, and/or with a second speed,
and while the disc performs one rotation, the vial holder performs one rotation in the opposite direction, thus keeping the absolute orientation of the vial holder constant while rotating. That is, the absolute orientation of the vial holder is always kept constant while rotating.

Preferably, the heating device comprises at least one heating sleeve surrounding the vial holder and/or the second stage gear.

Preferably, the heating device comprises or is associated with a least one temperature sensor associated with the heating sleeve, the vial holder and/or the sample, which detects the temperature of the heating sleeve, the vial holder and/or the sample and provides a corresponding signal.

Preferably, the control device comprises a time and/or step control device or function for controlling the driving device and/or the heating device.

Preferably, the control device comprises a driving control device or function, and/or a timing control device or function, and/or a temperature control device or function for controlling the driving device and/or the heating device.

Preferably, the control device is configured to control the driving device and/or the heating device at least in response to the signal provided by the temperature sensor.

Preferably, the transmitting device for inductive coupling for energy and/or signal transmission is configured to transmit the signal(s) provided by the temperature sensor to the control device.

The following preferred embodiments are part of all aspects of the present invention, in particular of the first, second, third and fourth aspect (and also of the aspects below, the fifth, the sixth, the seventh, the eighth, the ninth, the tenth, the eleventh and the twelfth aspect of the present invention).

The driving means or means for driving the disc preferably comprises a motor and a member which connects the motor with the disc, for example a tooth belt. That is, the disc is configured to be driven by means of a motor. Another implementation could be made by building the rotating disc in such a way that it can act as the rotor of a motor (adding a magnetic structure). In that case a stator built around the disc will complete the motor drive structure. This embodiment has the advantage of not needing any belt transmission or any drive gear.

The motor can be part of the apparatus for the automated lysis or can be provided as an additional component which is arranged outside of the apparatus. Since the apparatus is provided with a gear, one motor is sufficient for rotating the disc and the vial holder(s). However, it is also possible to provide a mechanism with which the disc and the vial holder(s) are driven in a separate manner, for example with separate motors. In this case, one of the gears (of the first or second stage) can be driven directly by an integrated motor. Also an external motor is usable.

The gears, embedded into the rotating disc, can also be built with more gear stages e.g. with four stages instead of two stages.

Each of the gears is preferably mounted within the disc by means of a bearing, preferably by means of a ball bearing, a bush bearing or a magnet bearing. Also the disc is pivot-mounted on the central pin by means of a bearing. The bearings reduce the friction, in particular since high rotation speeds are envisioned.

Further improvements are possible, for example with the use of vials having a specific configuration. Improvements in the efficiency of the lysis can be obtained not only when using vials with a circular cross-section, but also when using vials with a non-circular cross-section, in particular with an elliptic cross-section or with any uneven cross-section. That is, the vial holder should be for example formed in a manner that also such vials are receivable.

No modification of the vial holder(s) is necessary, if only the inner shape of a vial is formed in the specific manner as described above.

Vials with a cone-shaped bottom create efficient fluid and bead movements in an up-down direction.

For use in automated systems that allow loading and unloading of vials by a handling robot, the driving device, in particular the rotating disc, can preferably be equipped with or be associated with at least one position sensor allowing to detect exact start/stop positions of the vial holders. The position sensor is configured to detect a start position and/or a stop position of the disc and/or of the vial holder(s) (start/stop position detecting sensor). It is also possible to transmit the signals from the at least one position sensor by the means for inductive coupling, that is, the transmitting device.

The position sensors can also be associated with the at least one vial holder. That is, each vial holder can be provided with at least one position sensor.

Preferably, the vial holder is arranged substantially perpendicular to the disc or with an incline with respect to the disc. Therefore, the apparatus preferably comprises a deviation device which allows for arranging the vials inclined with respect to the disc (tangential deviation, non-right angle). The deviation device is configured to adjust the position of the vial holder, so that the vial holder is arranged substantially perpendicular to the disc or with an incline with respect to the disc. Such an arrangement can create a strong up and down movement of fluids, beads and sample materials during the rotation.

Preferably, the apparatus comprises at least two vial holders which are equally spaced on a circle on the disc. This will allow to easily balance the system and to avoid any mass imbalances. Providing more than two vial holders is also possible.

The incubation temperature is preferably in the range of 50° C. to 100° C., preferably at about 52° C., 53° C., 54° C., 55° C., 56° C., 57° C., 58° C., 59° C. and/or about 93° C., 94° C., 95° C., 96° C., 97° C., 98° C., more preferably at 56° C. and/or 96° C. For example an incubation temperature of 56° C. is used for the optimization of proteinase activity and additionally, an incubation temperature of 96° C. is used for the optimization for inactivating of the pathogens (without cooking).

The control device is preferably provided with a memory device and preferably with an input- and display device, so that an operator has the possibility to communicate with the apparatus and to input for example the conditions for the desired time and/or step control. The control device stores the conditions and runs the apparatus in the desired manner. The memory device and the input and display device can be provided as integrated devices (within the control device and/or the apparatus) or as additional devices.

The apparatus preferably comprises a device which allows for an additional up-down movement of the vial holder.

Due to the absence of strong vibrations, the integration of the individually rotatable disc and vial holder(s) into automated sample preparation systems becomes possible. With additional retaining elements on the vial holders it also is possible to mount the device in any arbitrary position (e.g. vertical).

In a fifth aspect, the present invention relates to a method for/of performing a lysis of a sample, in particular an automated and/or controlled lysis of a sample, in particular a biological sample, wherein the method comprises the steps of:
    rotating a disc and a vial holder for milling, grinding and mixing the sample during a rotating phase,
    heating the sample to at least one determined incubation temperature in a rotating phase and/or in a resting phase, maintaining the determined incubation temperature in a resting phase and/or in a rotating phase, and controlling the lysis, so that the steps are carried out by means of a timing and/or step control.

The wording "method for performing a lysis of a sample, in particular for performing an automated and/or controlled lysis of a sample" is interchangeable with the wording "method for lysing of a sample, in particular for automated and/or controlled lysing of a sample". This applies to all aspects of the present invention.

In a further step (or in further steps), cooling of the sample to at least one determined temperature can be carried out.

In a sixth aspect, the present invention relates to a method for performing a lysis of a sample, in particular for performing an automated and/or controlled lysis of a sample, in particular a biological sample, using the apparatus (or with or by means of the apparatus) according to the first aspect of the invention, wherein the method comprises the steps of:

rotating the disc and the vial holder for milling, grinding and mixing the sample during a rotating phase, heating the sample to at least one determined incubation temperature in a rotating phase and/or in a resting phase, maintaining the determined incubation temperature in a resting phase and/or in a rotating phase, and controlling the lysis, so that the steps are carried out by means of a timing and/or step control.

In a further step (or in further steps), cooling of the sample to at least one determined temperature can be carried out.

In a seventh aspect, the present invention relates to a method for performing a lysis of a sample, in particular for performing an automated and/or controlled lysis of a sample, in particular a biological sample, wherein the method comprises the steps of:

rotating a disc in a first direction and/or with a first speed, and rotating a vial holder in a second direction and/or with a second speed, for milling, grinding and mixing the sample during a rotating phase, heating the sample to at least one determined incubation temperature in a rotating phase and/or in a resting phase, maintaining the determined incubation temperature in a resting phase and/or in a rotating phase.

In a further step (or in further steps), cooling of the sample to at least one determined temperature can be carried out.

In a eighth aspect, the present invention relates to a method for performing a lysis of a sample, in particular for performing an automated and/or controlled lysis of a sample, in particular a biological sample, using the apparatus (or with or by means of the apparatus) according to the second aspect of the invention, wherein the method comprises the steps of:

rotating the disc in a first direction and/or with a first speed, and rotating the vial holder in a second direction and/or with a second speed, for milling, grinding and mixing the sample during a rotating phase, heating the sample to at least one determined incubation temperature in a rotating phase and/or in a resting phase, maintaining the determined incubation temperature in a resting phase and/or in a rotating phase.

In a further step (or in further steps), cooling of the sample to at least one determined temperature can be carried out.

In a ninth aspect, the present invention relates to a method for performing a lysis of a sample, in particular for performing an automated and/or controlled lysis of a sample, in particular a biological sample, wherein the method comprises the steps of:

rotating a disc and a vial holder for milling, grinding and mixing the sample during a rotating phase, heating the sample to at least one determined incubation temperature in a rotating phase and/or in a resting phase, maintaining the determined incubation temperature in a resting phase and/or in a rotating phase, and transmitting energy for heating to the heating device.

In a further step (or in further steps), cooling of the sample to at least one determined temperature can be carried out.

In a tenth aspect, the present invention relates to a method for performing a lysis of a sample, in particular for performing an automated and/or controlled lysis of a sample, in particular a biological sample, using the apparatus (or with or by means of the apparatus) according to the third aspect of the invention, wherein the method comprises the steps of:

rotating the disc and the vial holder for milling, grinding and mixing the sample during a rotating phase, heating the sample to at least one determined incubation temperature in a rotating phase and/or in a resting phase, maintaining the determined incubation temperature in a resting phase and/or in a rotating phase, and transmitting energy for heating to the heating device.

In a further step (or in further steps), cooling of the sample to at least one determined temperature can be carried out.

In a eleventh aspect, the present invention relates to a method for performing a lysis of a sample, in particular for performing an automated and/or controlled lysis of a sample, in particular a biological sample, wherein the method comprises the steps of:

rotating a disc and a vial holder for milling, grinding and mixing the sample during a rotating phase, heating the sample to at least one determined incubation temperature in a rotating phase and/or in a resting phase, maintaining the determined incubation temperature in a resting phase and/or in a rotating phase, and controlling the lysis, so that the steps are carried out by means of a timing and/or step control, and/or transmitting energy for heating to the heating device, and/or wherein the step of rotating the disc and the vial holder comprises the steps of:

rotating the disc in a first direction and/or with a first speed, and rotating the vial holder in a second direction and/or with a second speed, for milling, grinding and mixing the sample during a rotating phase.

In a further step (or in further steps), cooling of the sample to at least one determined temperature can be carried out.

In a twelfth aspect, the present invention relates to a method for performing a lysis of a sample, in particular for performing an automated and/or controlled lysis of a sample, in particular a biological sample, using the apparatus (or with or by means of the apparatus) according to the fourth aspect of the invention, wherein the method comprises the steps of:

rotating the disc and the vial holder for milling, grinding and mixing the sample during a rotating phase, heating the sample to at least one determined incubation temperature in a rotating phase and/or in a resting phase, maintaining the determined incubation temperature in a resting phase and/or in a rotating phase, and controlling the lysis, so that the steps are carried out by means of a timing and/or step control, and/or transmitting energy for heating to the heating device, and/or wherein the step of rotating the disc and the vial holder comprises the steps of:

rotating the disc in a first direction and/or with a first speed, and rotating the vial holder in a second direction and/or with a second speed, for milling, grinding and mixing the sample during a rotating phase.

In a further step (or in further steps), cooling of the sample to at least one determined temperature can be carried out.

The wording "method for performing a lysis of a sample, in particular for performing an automated or controlled lysis of a sample" is interchangeable with the wording "method for lysing of a sample, in particular for automated or controlled lysing of a sample".

All the preferred embodiments of the first aspect of the present invention are also part of the other aspects, that is, of the second, the third, the fourth, the fifth, the sixth, the seventh, the eighth, the ninth, the tenth, the eleventh and the twelfth aspect of the present invention.

Due to the cooperation of the driving device and the control device, in particular due to the cooperation of the gear (for example planetary gear) and the time and/or step control, the apparatus is able to perform an automated and/or controlled lysis or lysis procedure in an efficient, effective and in a safe manner. Furthermore, due to the determined sequence control (time and/or step control), and the improved conditions (for example higher acceleration) the high efficiency of the lysis does not depend on the composition of the sample. Every kind of sample can be processed in an efficient and effective manner.

The driving unit or device is also referred to for example as a disc and/or vial holder driving unit or device, the heating device is also referred to for example as a sample heating device, and the control unit is also referred to for example as a driving device and heating device control unit.

Additional preferred embodiments, advantages and features of the present invention are defined in the dependent claims and/or will become apparent by reference to the following detailed description and the accompanying drawings.

DETAILED DESCRIPTION OF PREFERRED EMBODIMENT

The present invention will now be further described by defining different aspects of the invention generally outlined above in more detail. Each aspect so defined may be combined with any other aspect or aspects unless clearly indicated to the contrary. In particular, any feature indicated as being preferred or advantageous may be combined with any other feature or features indicated as being preferred or advantageous.

The drawings are not necessarily to scale. In certain instances, details that are not necessary for an understanding of the embodiment or that render other details difficult to perceive may have been omitted.

The same or equally acting components are provided with the same reference signs.

The term "lysis" describes the disintegration of biological cells to allow access to the cellular constituents.

The term "sample" as used herein includes any reagents, solids, liquids, and/or gases.

The term "cell" includes human, animal and plant cells (including bacteria and fungi).

Figure 1:
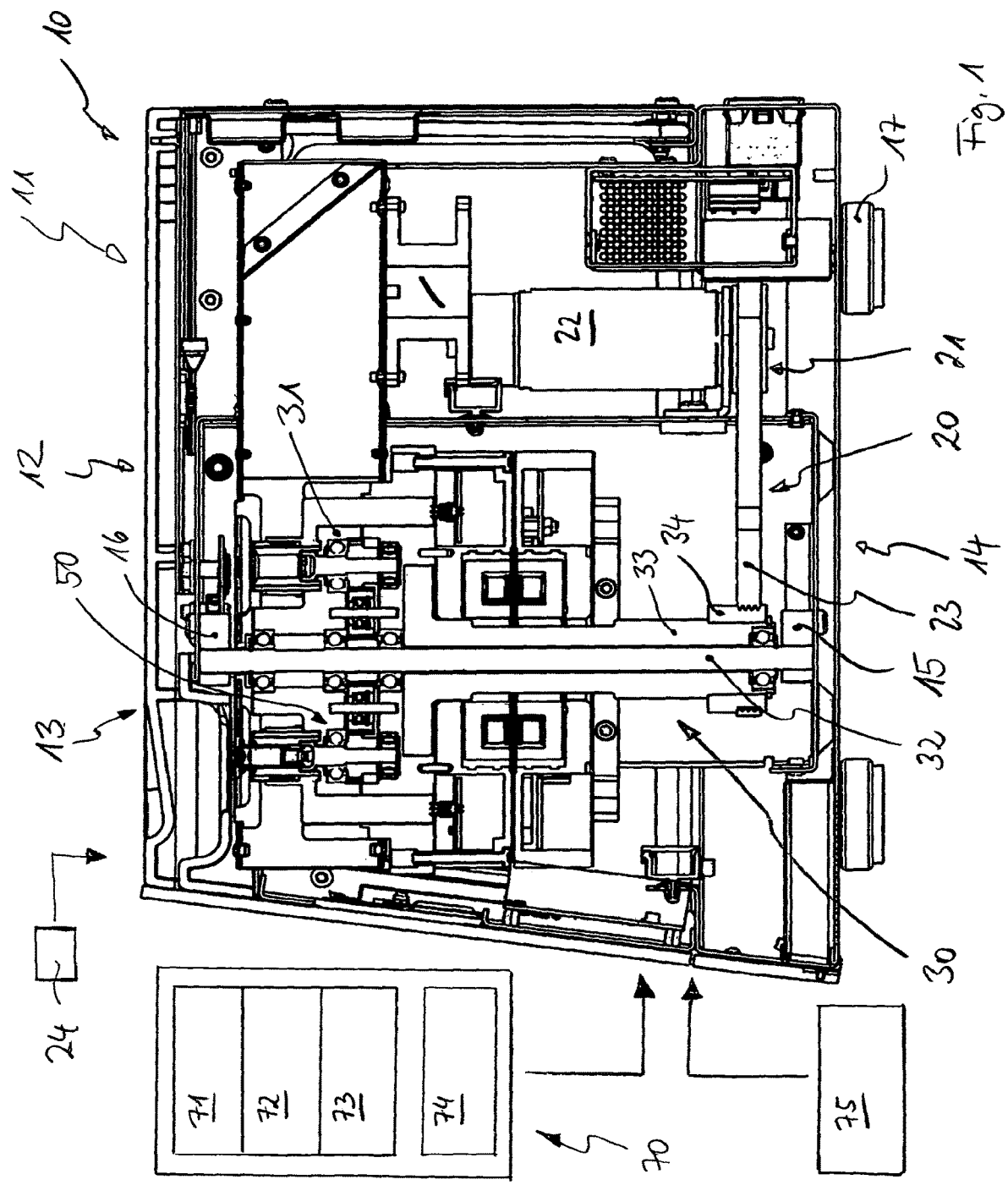
FIG. 1 depicts a schematic cross-sectional side view of the apparatus according to a preferred embodiment of the present invention.

FIG. 1 shows schematically and not to scale an apparatus 10 for automated or controlled lysis of a sample, in particular a biological sample. The apparatus 10 allows for sample homogenization, cell and tissue lysis and the mixing of reagents. Therefore, the apparatus 10 performs or is configured to carry out steps like vortexing, grinding and milling of the sample within a vial holder and also the step of heating the sample and keeping the vial holder and therefore the sample in a resting phase.

Figure 2:
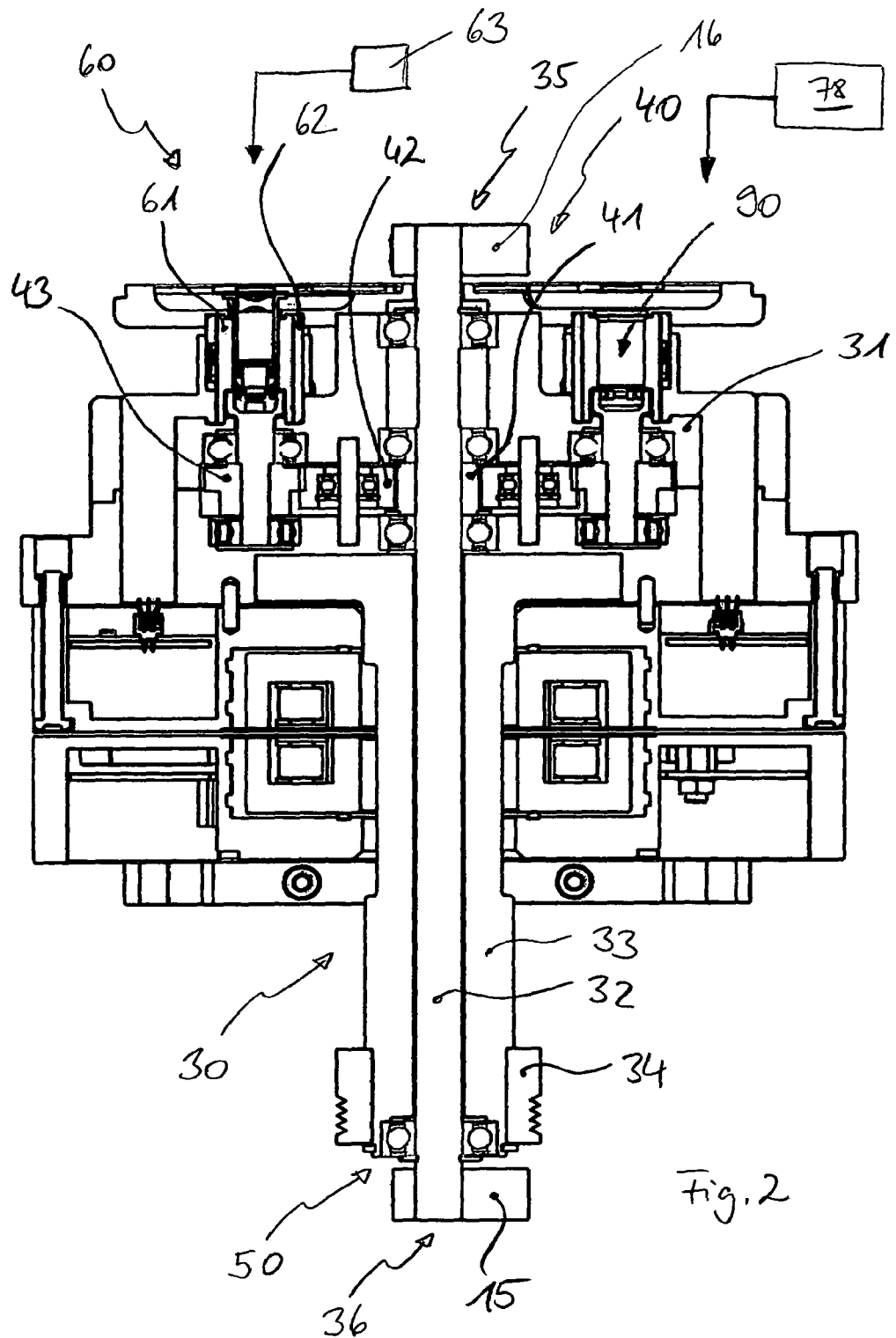
FIG. 2 depicts a schematic cross-sectional view of a disc, a gear and a central pin (at least a part of a rotating device) of the embodiment of FIG. 1.

FIG. 2 depicts a schematic cross-sectional view of a disc 31, a gear 40 and a central pin 32 (rotating device 30) of the embodiment of FIG. 1, that is, a part of the device shown in FIG. 1 is depicted in an enlarged view. Vortexing (mixing), grinding and milling steps are carried out by means of the rotating device 30.

The lysis apparatus 10 in this preferred embodiment comprises a housing 11 including a lid 13 which allows for inserting one or more vials 100 (see FIG. 4), containing the sample, into the apparatus 10. The lid is for example arranged at a top side 12 of the housing 11, or the lid 13 forms the top side 12 of the housing 11 (as shown in this embodiment). The lid is configured to be removable, for example by means of a sliding mechanism (thereby using for example a motor). A bottom side 14 is formed as a bottom plate, comprising foot members 17, in order to position the apparatus 10 on a desired location. The rotation disc 31 (see FIG. 3) and four vial holders 90 (see FIG. 4) for receiving vials 100 are provided, wherein the vial holders 90 are connected with the disc 31. The disc 31 and the vial holders 90 are rotatable by means of a driving device 20. Furthermore, a heating device 60 is provided, for heating the samples within the vials 100, received in the vial holder 90 (see FIG. 2).

In particular FIG. 2 shows the heating device 60 for heating the sample within the vials 100. The heating device 60 comprises a heater 61 which is configured as a heating sleeve surrounding the vial holder (each of the vial holders 90 is surrounded by a heating sleeve). A thermal insulation member 62 insulates the heater 61 from the environment. The heating device is associated with at least one sensor 63. The sensor 63 is associated with the sleeve 61, the vial holder 90 and/or with the sample, and detects the temperature of the heating sleeve, the vial holder and/or the sample. In this embodiment each vial holder is provided with one sensor (merely one sensor is shown).

For use in automated systems that allow loading and unloading of vials by a handling robot, the rotating disc can be equipped with a position sensor 24 (see FIG. 1) allowing for adjusting, controlling and/or detecting exact start/stop positions for the vial holders (and/or of the disc).

The disc 31 is pivot-mounted on the central pin 32, wherein the pin 32 as a non-rotating element is fixed with a base member (base plate) 15 and a cover member (cover plate) 16, mounted within the housing 11, near the bottom side 14 and the top side 12. In this embodiment, the pin 32 is configured as an elongated member, arranged perpendicular to the bottom side 14, extending from the bottom side 14 to the top side 12 of the apparatus. The disc 31 with the vial holders 90 is provided on a first end 35 of the central pin or member 32 (in use near the top side 12 of the apparatus 10). On a second end 36, opposite the first end 35 (in use near the bottom side 14), the pin 32 is connected to the base member 15.

The driving device 20 comprises driving means 21 for driving the disc 31. The driving means 21 include a motor 22—in this embodiment arranged within the apparatus 10—and for example a tooth belt 23 for connecting the motor 22 with the disc 31.

A sleeve 33, surrounding the pin 32 and pivot-mounted on the pin 32 by means of bearings is connected with the disc 31 (supports the disc). Additionally, the sleeve 33 comprises a member 34 for engaging the tooth belt 23, that is, for example a toothed pulley 34. In an alternative, a V-belt and a V-belt pulley can be used. That is, in this embodiment, the belt 23 does not directly engage the disc 31, but does engage the pulley 34 and the sleeve 33 which is connected with the disc 31. The sleeve 33 can be built integral with the disc 31 or can be provided as separate element which is connected to the disc.

As an alternative, it is also possible to arrange the belt for example directly on the disc (the belt engages the disc), for example on the circumference of the disc.

The driving device 20 furthermore comprises the gear 40, in this embodiment arranged within the disc 31. The disc 31 therefore defines a carrier plate. The gear 40, for example a planetary gear, comprises (in this embodiment) a central pinion (central wheel) 41 which is fixed on the central pin 32 and is therefore a non-rotating element. Furthermore, first stage gears (or gear wheels) 42 and second stage gears (or gear wheels) 43 are provided, wherein the vial holders 90 are associated with or connected with the second stage gears 43. Since this embodiment comprises four vial holders 90, there are also provide four first stage gears and four second stage gears, which are equally spaced on a circle on the rotating disc 31. The first stage gears 42 are driven via the disc 31 by the central pinion 41, and the second stage gears 43 are driven by the first stage gears 42.

The disc 31, the central pin 32 with the sleeve 33, and the gear 40 defining a rotating device 30 which is driven by means of the driving means 21. The rotatable components are pivot-mounted by means of one or more bearings 50 (the Figs. show roller bearings) to reduce the friction between the components.

A control device 70 (see FIG. 1) controls the operation of the driving device 20 and/or the heating device 60 in such a manner that the driving device 20 and the heating device 60 work or operate in a coordinated manner, preferably by means of a timing and/or step control. Thus, the lysis procedure runs in an automated manner, since the single steps of the lysis (for example vortexing, grinding and/or milling of the sample within the vial holder and also the steps of heating the sample(s) and keeping the vial holder and therefore the sample in a resting phase), are automatically controlled. The control device initiates (starts) and stops the single steps at a desired or determined point of time (determines and/or adjusts the duration of the single steps), determines and/or adjusts the direction and the speed of the rotation of the components (for example of the disc) and determines and/or adjusts the temperatures which have to be achieved (incubation temperatures).

The control device 70 is part of the apparatus or can be provided as a single device being associated with the apparatus and the corresponding components, respectively. In FIG. 1, the control device 70 is indicated as a black box. The control device 70 comprises for example a driving control device or function 71, and/or a timing control device or function 72, and/or a temperature control device 73 or function for controlling the driving device 20 and the heating device 60.

The driving control device controls for example the direction of rotation of the disc and the speed during the rotation, the timing control device controls for example the duration of the rotating phase and of the resting phase and the temperature or heating control device controls for example the temperature of the sample, the vial holder and/or the heating element (for example the heating sleeve).

Therefore, the control device can be provided as a timing and/or step control device or can be provided with this function for controlling the driving device 20 and the heating device 60.

The control device is advantageously provided with a memory device 74 and with an input and/or display device 75 to allow for communication between an operator/user and the apparatus. The control device stores input data provided by the operator via the input device within the memory device and runs the apparatus in the desired manner. Also predetermined control processes or courses can be stored in the memory device and can be used during operation. The memory device and the input and display device can be provided as integrated devices (within the control device and/or the apparatus) or as additional devices.

The energy and/or measurement signal transmission is provided by a transmitting device 80 for inductive coupling for energy and/or signal transmission, that is, by a transmitting device 80 for transmitting energy and/or signals, in cooperation with the control device 70. The energy for heating the heating sleeve(s) is provided by means of the transmitting device 80 (inductive coupling), and the energy is for example used to heat at least one wire associated with each of the sleeves (for example in case of resistance heating). Also the signal of the temperature sensor (that is, the measured temperature, measured by the temperature sensor) is transmitted to the control device 70 by means of the transmitting device 80 (due to inductive coupling) for the further control procedure, that is, for example feedback control.

Figure 3:
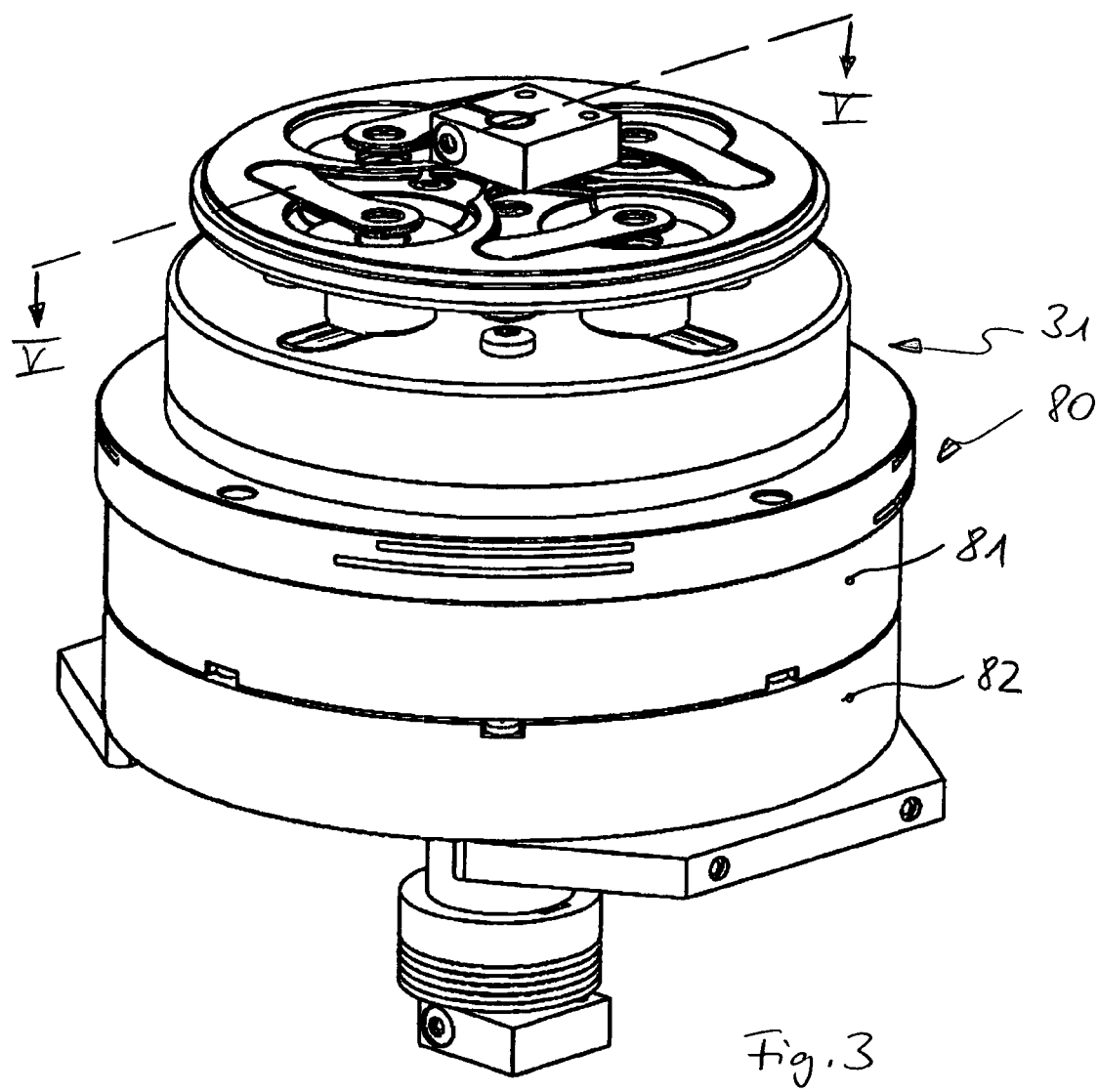
FIG. 3 depicts a perspective schematic view of a part of the rotating device of the embodiment of FIG. 1.

FIG. 3 depicts a perspective schematic view of at least a part of the rotating device of the embodiment of FIG. 1. The Fig. shows the disc 31 with the transmitting device 80 (means for inductive coupling for energy and signal transmission, inductive transducer) which comprises a rotating part 81, connected with the disc 31 and a fixed part 82.

The apparatus furthermore comprises for example a deviation device 78 (see FIG. 2) which allows for arranging the vials inclined with respect to the disc (tangential deviation, non-right angle, tilting the axis of the vial holder relative to the axis of the disc 31). The device is preferably integrated within the apparatus, that is, part of the apparatus.

Figure 4:
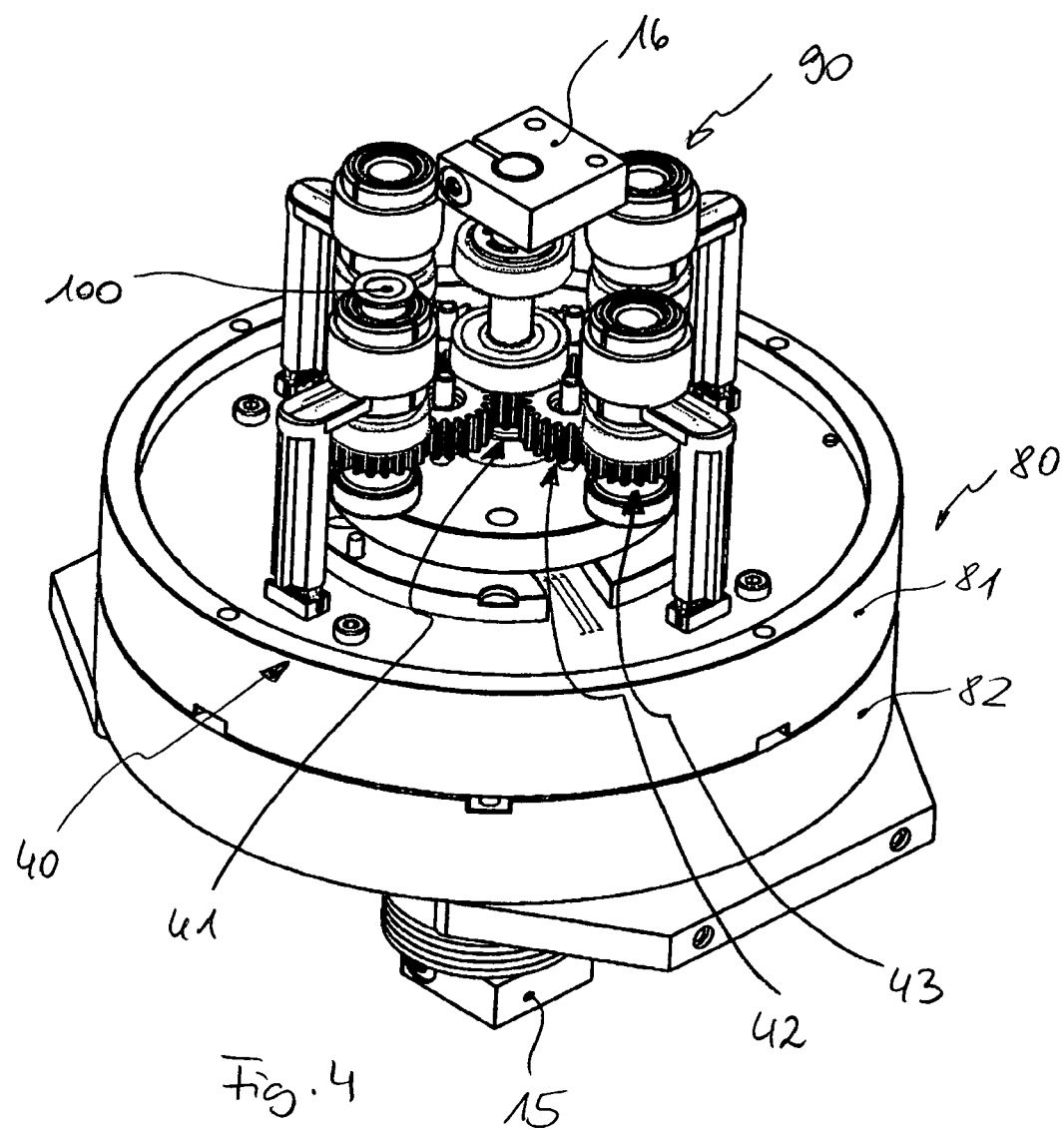
FIG. 4 depicts a further perspective schematic view of a part of the rotating device of the embodiment of FIG. 1.

FIG. 4 depicts a further perspective schematic view of at least a part of the rotating device 30 of the embodiment of FIG. 1, without the disc 31. Merely the transmitting device 80 is shown. Therefore, the gear 40 can be seen. The four vial holders 90 are arranged above the four second stage gear wheels 43. One of the vial holders 90 contains a vial 100.

Figure 5:
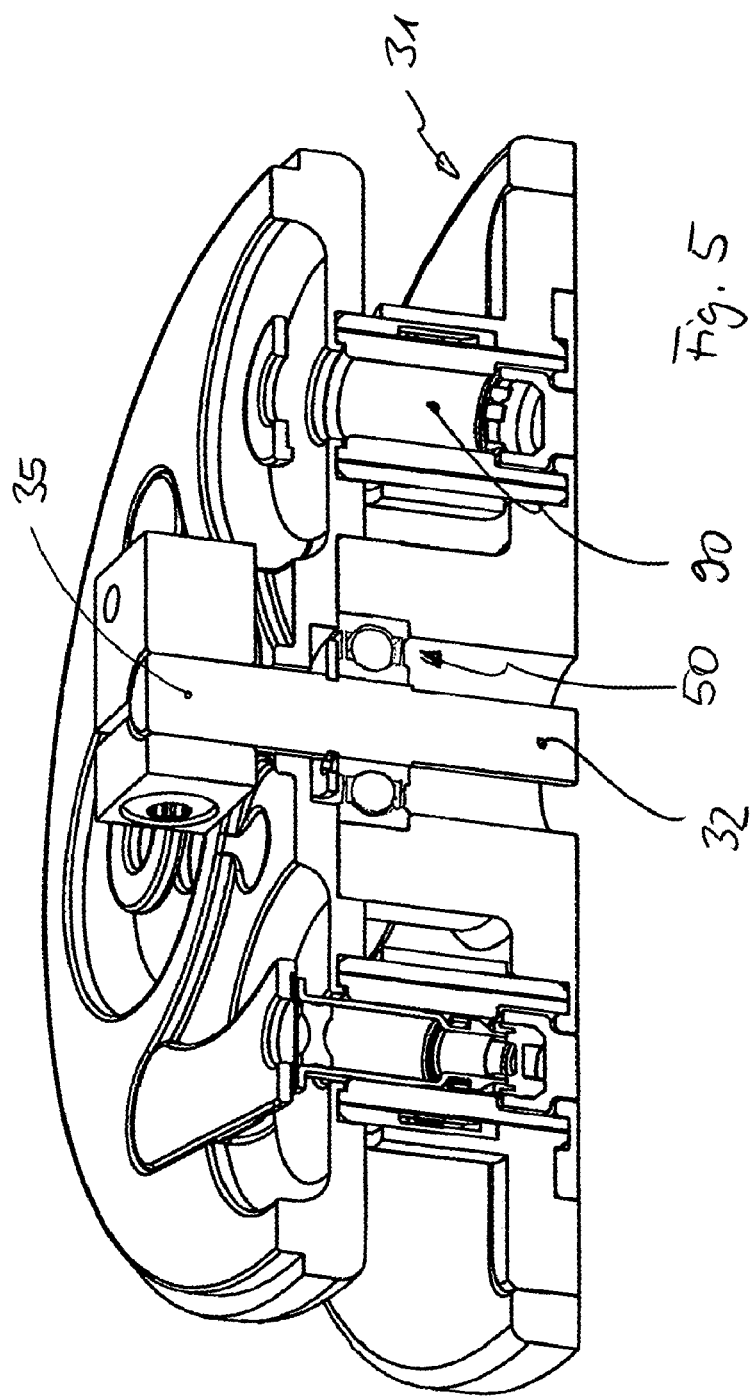
FIG. 5 depicts a perspective schematic sectional view of a part of the rotating device, along the line V-V in FIG. 3

FIG. 5 depicts a perspective schematic sectional view of a part of the rotating device 30, along the line V-V in FIG. 3.

Figure 6:
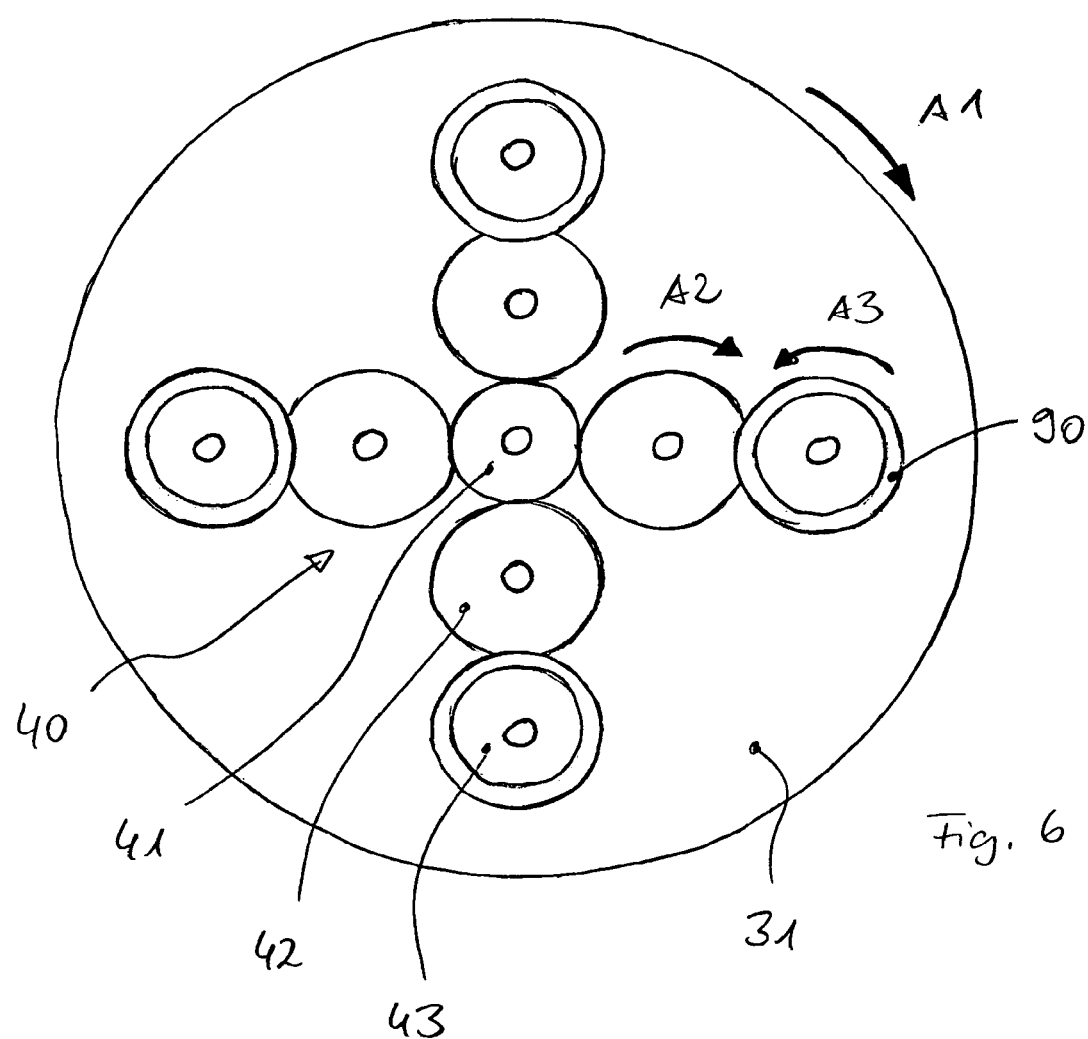
FIG. 6 depicts a simplified top view of the driving disc and the gear of the embodiment of FIG. 1.

Having described the main structural features of the apparatus 10 for automated lysis of a sample, in particular a biological sample according to the present invention, the below will describe under further reference to FIG. 6 (simplified top view of the rotating disc 31 and the gear 40 of the embodiment of FIG. 1) the function of the apparatus 10 during a lysis procedure. The apparatus 10 allows for sample homogenization, cell and tissue lysis and the mixing of reagents.

In order to perform the lysis of a sample, the sample has to be filled into a vial, which is configured to be received in the vial holder 90. In the embodiment described with the FIGS. 1 to 5, four vials can be inserted into the four vial holders 90.

The motor 22 drives the disc 31 via the tooth belt 23 and the sleeve 33 with the pulley 34 pivot mounted on the central pin 32 for example in a clockwise direction A1 (first direction). The rotation of the disc 31 now drives the gear 40 via the central non-rotating pinion, in such a manner that the first stage gears 42 also rotate in the clockwise direction A2 (first direction). Thus, the second stage gears 43 rotate in a counterclockwise direction A3 (second direction). Rotating the gear wheels in an opposed direction allows for a very efficient and effective lysis procedure, in particular with the heating of the sample.

The control device 70 controls the driving device 20 for example such that while the rotation disc 31 performs one rotation, the vial holder(s) 90 perform(s) one rotation in the opposite direction, thus always keeping the absolute orientation of the vial holder(s) 90 substantially constant while rotating (balanced masses in comparison with a conventional vortexer or vortexing device). Due to the superimposed circular movements of the disc 31 and the vial holders 90 in that specific manner, the system is balanced and runs in a very smooth manner.

If e. g. the second stage gear has more teeth or fewer teeth than the center fixed pinion, the vial holders in addition perform a rotational movement superimposed to the original movement with a rotational speed determined by the ratio of the number of teeth of the pinions. Such a superimposed (for example slow) rotation may help mixing the sample and fluids in the vials even better.

The gear ratio and therefore the speed of rotation and the direction of rotation (of the disc and the vial holder(s)) is definable in a desired manner, for example by means of the control device 70. Also other wheels can be used with another teeth ratio, or the gear can be provided with more stages. Other kinds of gears are also applicable.

Energy for heating the sleeve(s) 61 is transmitted by the transmitting device 80, that is, by means of inductive coupling (energy and signal transmission). The sleeve is for example configured as resistance heating, and the required energy is transmitted by the transmitting device 80. The transmitting device 80 for inductive coupling is also configured to allow for transmission of the signals, in particular for transmission of the temperature value determined by the temperature sensor(s). Thus, the control device, receiving the measured values from the sensor(s), controls the lysis procedure at least by means of the measured temperature value(s), see also the above provided example of a protocol with the steps a) to h). Therefore, due to the feedback a time and/or step control is carried out.

The controllable driving device 20 and the controllable heating device 60 allow for an automated lysis procedure by means of the apparatus 10 described above. Since the control device 70 operates the apparatus 10 by means of a time and/or step control, the single steps of vortexing and mixing, respectively, grinding, milling, heating and keeping the vial holder (and thus, the sample) in a resting phase, the adjustment of rotation speed, rotation direction and temperature and the adjustment of the duration of each step are carried out by means of a defined and/or determined (or predetermined) schedule or workflow. Therefore, the lysis is executed automatically, without the need of interruptions and without the need of well trained users controlling the several steps.

Since the apparatus is configured in the above described manner (balanced masses) higher velocities and an increased acceleration are possible (in comparison with conventional devices). Due to the transmitting device, energy and/or signals can be transmitted in a desired manner without the need of wires etc. Therefore, the high rotation speeds can be carried out.

The invention can combine the following aspects:
providing a control device which is configured to control the steps of the lysis by means of a timing and/or step control;
providing a specific arrangement of the apparatus, which allows for a specific movement of the vial holder(s) and thus, providing a system with balanced masses;
providing a transmitting device (means for inductive coupling) for energy and/or signal transmission.

The above described invention can be used for any application where biological or other material samples (chemistry, food processing, . . . ) need to undergo a bead milling procedure to homogenize the material and/or to effectively mix fluids or suspensions of highly different viscosity. In particular, the invention is used to build more effective and more robust bead mills and vortexers.

LIST OF REFERENCE SIGNS

10 apparatus for (automated and/or controlled) lysis
11 housing
12 top side
13 lid
14 bottom side
15 base member, base plate
16 cover member, cover plate
17 foot member
20 driving device
21 driving means
22 motor
23 tooth belt
24 position sensor
30 rotating device
31 disc
32 central pin
33 sleeve
34 pulley
35 first end of the pin
36 second end of the pin 40 gear
41 central pinion
42 first stage gear
43 second stage gear
50 bearing, roller bearing
60 heating device
61 heater, heating sleeve
62 insulation member
63 temperature sensor
70 control device
71 driving control device
72 timing control device
73 heating or temperature control device
74 memory device
75 input/display device
78 deviation device
80 transmitting device
81 rotating part
82 fixed part
90 vial holder
100 vial
A1 first direction (disc)
A2 first direction (first stage gear)
A3 second direction (second stage gear)

The invention claimed is:

1. An apparatus for lysis of a sample, the apparatus comprising:
 a rotation disc;
 a vial holder configured to receive a single vial, wherein the vial holder is arranged on the rotation disc;
 a driving device comprising a motor and a gear set, wherein the gear set comprises a first stage gear and a second stage gear driven by the first stage gear, wherein the vial holder and second stage gear share a common central axis and wherein the driving device is configured to rotate the rotation disc in a first direction and the vial holder in a second direction such that the vial holder is maintained in a substantially constant absolute orientation while rotating; and
 a heater engaged with the vial holder and configured to heat the sample to a determined incubation temperature.

2. The apparatus of claim 1, wherein the driving device further comprises a central pin to which the rotation disc is pivot-mounted and a central pinion fixed on the central pin.

3. The apparatus of claim 2, wherein the first stage gear is driven via the rotation disc by the central pinion.

4. The apparatus of claim 1, wherein the gear set comprises a planetary gear.

5. The apparatus of claim 1, further comprising a control device in communication with the motor and with the heater and configured to control the motor and the heater according to input data and a protocol to be carried out automatically according to at least one of time control, step control, or feedback control, wherein feedback control is based on a signal received from at least one of a position sensor or a temperature sensor.

6. The apparatus of claim 5, wherein the protocol comprises a rotating phase and a resting phase.

7. A method for performing a lysis of a sample using the apparatus of claim 6, wherein the method comprises:
 rotating the rotation disc and vial holder for milling, grinding and mixing the sample during the rotating phase,
 heating the sample to the determined incubation temperature in the rotating phase and/or in the resting phase, and
 maintaining the determined incubation temperature in the resting phase and/or in the rotating phase.

8. An apparatus for lysis of a sample, the apparatus comprising:
 a motor;
 a rotation disc engaged with the motor, wherein the rotation disc is configured to rotate in a first direction;
 a gear set engaged with the rotation disc, wherein the gear set comprises a first stage gear and a second stage gear, the first stage gear being engaged with the rotation disc;
 a vial holder configured to receive a single vial, wherein the second stage gear is engaged with the first stage gear and the vial holder and wherein the vial holder and second stage gear share a common central axis, such that the vial holder is rotatable in a second direction opposite the first direction and is maintained in a substantially constant absolute orientation while the rotation disc rotates; and
 a heater engaged with the vial holder, wherein the heater is configured to heat the sample to a determined incubation temperature.

9. The apparatus of claim 8, wherein the heater comprises at least one heating sleeve surrounding at least one of the vial holder or the second stage gear.

10. The apparatus of claim 9, wherein the heater comprises or is associated with at least one temperature sensor associated with at least one of the heating sleeve or the vial holder; wherein the temperature sensor detects a temperature of at least one of the heating sleeve or the vial holder; and wherein the temperature sensor provides a signal corresponding to the temperature of at least one of the heating sleeve or the vial holder.

11. The apparatus of claim 8, further comprising a control device in communication with the motor and with the heater and configured to control the motor and the heater according to input data and a protocol to be carried out automatically according to at least one of time control, step control, or feedback control, wherein feedback control is based on a signal received from at least one of a position sensor or a temperature sensor.

12. The apparatus of claim 11, wherein the protocol comprises a rotating phase and a resting phase.

13. The apparatus of claim 11, wherein the rotating phase comprises rotating the rotation disc and the vial holder for milling, grinding, and mixing a sample.

14. The apparatus of claim 13, wherein the protocol comprises heating the sample to a determined incubation temperature in the rotating phase.

15. The apparatus of claim 14, wherein the protocol comprises maintaining the determined incubation temperature in the rotating phase.

16. The apparatus of claim 13, wherein the protocol comprises heating the sample to a determined incubation temperature in the resting phase.

17. The apparatus of claim 16, wherein the protocol comprises maintaining the determined incubation temperature in the resting phase.

18. An apparatus for lysis of a sample, the apparatus comprising:
 a motor;
 a rotation disc engaged with the motor, wherein the rotation disc is configured to rotate in a first direction;
 at least one gear set engaged with the rotation disc, wherein each such gear set consists of a first stage gear engaged with a second stage gear;
 a vial holder configured to receive no more than one vial, wherein the vial holder is associated with the second stage gear and wherein the vial holder and the second stage gear share a common central axis; and a heater engaged with the vial holder, wherein the heater is configured to heat the sample to a determined incubation temperature;

wherein the vial holder is rotatable in a second direction opposite the first direction and is maintained in a substantially constant absolute orientation while the rotation disc rotates.

19. The apparatus of claim 18, wherein the heater comprises at least one heating sleeve surrounding at least one of the vial holder or the second stage gear.

* * * * *